US005849579A

United States Patent [19]

Li

[11] Patent Number: 5,849,579

[45] Date of Patent: Dec. 15, 1998

[54] NATIVE-STATE HISTOCULTURING METHOD FOR SKIN

[75] Inventor: Lingna Li, La Jolla, Calif.

[73] Assignee: Anticancer, Inc., San Diego, Calif.

[21] Appl. No.: 642,322

[22] Filed: May 3, 1996

Related U.S. Application Data

[63] Continuation of Ser. No. 129,022, Sep. 29, 1993, which is a continuation of Ser. No. 662,239, Feb. 28, 1991, abandoned.

[51] Int. Cl.[6] .......... C12N 5/00

[52] U.S. Cl. .......... 435/325; 435/4; 435/395; 435/399; 623/15

[58] Field of Search .......... 435/240.2, 4, 325, 435/399, 395; 623/15

[56] References Cited

U.S. PATENT DOCUMENTS

| | | |
|---|---|---|
| 4,508,819 | 4/1985 | Rose . |
| 4,537,790 | 8/1985 | Horodniceanu et al. . |
| 4,910,142 | 3/1990 | Schwengers et al. . |
| 4,919,664 | 4/1990 | Oliver et al. . |
| 4,940,853 | 7/1990 | Vandenburgh . |
| 4,963,489 | 10/1990 | Naughton et al. . |
| 4,963,490 | 10/1990 | Churchouse et al. . |
| 4,994,388 | 2/1991 | Hillegas et al. . |
| 4,996,154 | 2/1991 | Gabriels, Jr. . |
| 5,015,584 | 5/1991 | Brysk . |

OTHER PUBLICATIONS

Boyce et al., *Surgery,* vol. 103(4), pp. 421–431 (1988).
Douglas et al., *In Vitro,* vol. 16(4), pp. 306–312 (1980).
Frater et al., *J. Invest. Dermatol.*, 61:72–81 (1973)
Kao et al., *Toxicol. Appl. Pharmacol.*, 81:502–516 (1985)
Leighton, *J. Natl. Cancer Inst.* , 12:545–561 (1951)
Van Brunt, *Bio/Technol.*, 9:136–137 (1991)
Boyce et al., *Surgery*, vol. 103(4), pp. 421–431 (1988)
Douglas et al., *In Vitro*, vol. 16(4), pp. 306–312 (1980)

*Primary Examiner*—Leon B. Lankford, Jr.
*Attorney, Agent, or Firm*—Morrison & Foerster LLP

[57] ABSTRACT

Methods and compositions for a native-state histoculturing system for skin are disclosed. Skin samples are placed on an extracellular support matrix immersed in a medium whereby the internal surface of the skin is adjacent to the matrix and the external surface is exposed above the surface of the medium and the skin maintained in the medium under skin culturing conditions. An extracellular support matrix comprising a collagen-containing gel and homopolysaccharide sponge or a combination matrix of a top layer of a collagen-containing gel and a bottom layer of a homopolysaccharide sponge is also disclosed. Skin toxicity, hair growth, anti-aging and anti-wrinkling assays utilizing the histoculturing system of the present invention are also disclosed.

13 Claims, 7 Drawing Sheets

NATIVE-STATE HISTOCULTURING METHOD FOR SKIN

This application is a continuation of application Ser. No. 08/129,022 filed Sep. 29, 1993, which is a continuation of application Ser. No. 07/662,239 filed Feb. 28, 1991 now abandoned.

DESCRIPTION

1. Technical Field of the Invention

The present invention relates to a method of native-state histoculturing skin and to assays utilizing such method.

2. Background of the Invention

All commercial products that contact the skin (i.e., cosmetics, household products and pharmaceuticals) must undergo extensive testing to ensure that such products are not toxic to humans. Currently available means for evaluating the toxicity of such products are expensive, time-consuming and often involve exposing large numbers of live animals to toxic substances. The use of live animals for such toxicity testing has come under increasing criticism and scrutiny by the public, the scientific community and the government. There is a pressing need to develop skin toxicity assays which obviate the exposure of live animals to toxic substances.

Although a number of attempts to develop in vitro assays for skin toxicity have recently been reported, such systems have proven inadequate for accurately and reliably predicting the toxic effects of substances on natural skin. Many of these in vitro assays involve culturing individual cells, which have been isolated from the skin of subject animals. See. e.g., Van Brunt, J., *Biotechnology,* 9: 136–137 (1991) and Naughton et al., Alternative Methods In Toxicology, ed. by A. M. Goldberg, 7: 183–189 (1989). Such assays based on cell culture are over simplified and inadequate, especially where putative toxins exert their effect by altering cell to cell interactions.

The model of Naughton et al. involves isolating skin fibroblasts from dermal tissue, growing such isolated fibroblasts in an appropriate medium, plating the fibroblasts onto a nylon mesh, isolating malanocytes from another skin sample, culturing such isolated malanocytes, plating the cultured malanocytes onto a fibroblast-coated nylon mesh, isolating keratinocytes and plating the isolated keratinocytes onto the malanocyte-fibroblast-nylon mesh. Not only does such a system lack an equivalence to natural skin, the use of such a technique involves the time-consuming steps of isolating of at least three different cell types, culturing each cell type individually and then co-culturing the individual cell types together on a nylon mesh. According to the authors, the minimum time required for establishment of this system ranges from about 8 to about 14 days.

In a similar fashion, other in vitro systems currently available or under development utilize individually cultured cells rather than intact skin. In some cases, cells from different organisms are combined into a single skin equivalent. Van Brunt, supra.

One laboratory has tried to establish a culturing system for intact skin, but failed to maintain skin viability for more than 24 hours. Kao et al, *Toxicology and Applied Pharmacology,* 81:502–516 (1985).

Despite the expenditure of time and energy by the academic and industrial scientific communities, there is no currently available skin histoculturing system, which allows cultured skin to remain viable and grow while maintaining native-state, three-dimensional architecture for prolonged times.

The present invention provides such a long-term, native-state histoculturing system for skin and, thus, provides a solution to the pressing and long-felt need for such a system.

SUMMARY OF THE INVENTION

The present invention provides a method of native-state histoculturing a skin sample having internal and external surfaces comprising placing the skin sample on an extracellular support matrix immersed in a medium whereby the internal surface is adjacent to the matrix and the external surface is exposed above the surface of the medium and maintaining the matrix with the skin thereon under skin culturing conditions.

The extracellular support matrix is preferably a collagen-containing gel, a homopolysaccharide sponge or a combination matrix comprising a top layer of a collagen-containing gel and a bottom layer of a homopolysaccharide sponge. The collagen-containing gel is preferably gelatinized pork skin and the homopolysaccharide is preferably cellulose.

The sample of skin utilized in accordance with the present invention is preferably of mammalian origin and, more preferably of human origin.

The present invention further provides an extracellular support matrix for native-state histoculturing skin comprising a top layer of a collagen-containing gel and a bottom layer of a homopolysaccharide sponge.

Still further, the present invention provides a skin toxicity assay comprising the steps of (a) culturing a skin sample having internal and external surfaces on an extracellular support matrix immersed in a medium under skin culturing conditions whereby the internal surface is adjacent to the matrix and the external surface is exposed above the surface of the medium, (b) contacting the skin sample with a putative toxin, (c) maintaining the skin sample and matrix in the presence of the toxin for a preselected period of time, and (d) assessing the viability of the skin sample and thereby the skin toxicity of the toxin.

Viability is assessed by measuring the incorporation into cells of the skin sample of an indicator specific for viable or dead cells. The indicators are preferably dyes capable of optical detection and, more preferably fluorescent dyes. Alternatively, viability is assessed by adding a first dye specific for cell viability and a second dye specific for dead cells to the medium, maintaining the dye-containing medium for a preselected period of time, and optically scanning the skin sample to quantify distribution of the first and second dyes in the skin sample and thereby assessing toxicity.

In a preferred embodiment, the skin toxicity assay further comprises assessing the viability of the skin sample prior to contacting the skin sample with a putative toxin and comparing the assessed viability before and after contact with the putative toxin and thereby the toxicity of the toxin.

The present invention also provides a hair growth assay comprising (a) culturing a skin sample capable of growing hair and having internal and external surfaces on an extracellular support matrix immersed in a medium whereby the internal surface is adjacent to the matrix and the external surface is exposed above the surface of the medium, (b) making a first determination of hair growth status, (c) maintaining the skin sample and matrix in the medium for a preselected period of time, (d) making a second determination of hair growth status, and (e) comparing the first and second determinations of hair growth status thereby determining hair growth.

Hair growth status is preferably a physical dimension of the hair such as hair length.

One advantage of the present invention is the provision of a histoculturing system for skin whereby the native-state, three-dimensional architecture of skin is maintained during culture.

Another advantage of the present invention is the provision of a simple, inexpensive and reliable skin toxicity assay for determining the effects of putative toxins on skin. Such an assay also provides an economically efficient means for evaluating in vitro, the affects of putative toxins, which assay does not involve exposing live animals to the toxins. The assay provides a model for studying cell viability and biochemical response in dermatological research and testing.

Yet another advantage of the present invention is the provision of a simple, inexpensive and reliable means for assessing hair growth in vitro and for measuring effects of compositions on hair growth.

BRIEF DESCRIPTION OF THE DRAWINGS

In the drawings forming a portion of this disclosure.

DETAILED DESCRIPTION OF THE INVENTION

A. A Native-State Histoculturing Method

Figure 1:
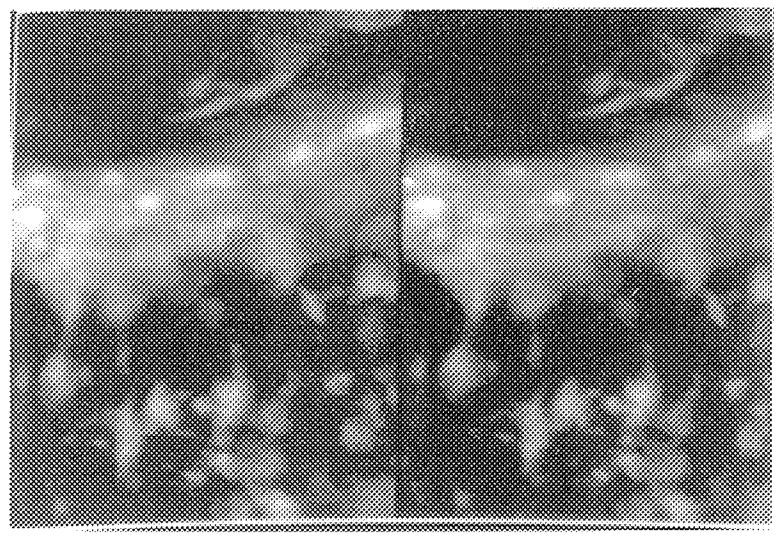
FIG. 1 is a colored photomicrograph depicting mouse skin histocultured for two days having been double-stained with BCECF-AM (green-live cells) and PI (red-dead cells)as described in Example 1. Confocal scanning laser microscopy. Magnification 1000× Stereo Image.

One aspect of the present invention relates to a method of native-state histoculturing a skin sample having internal and external surfaces comprising placing the skin sample on an extracellular support matrix immersed in a medium whereby the internal surface is adjacent to the matrix and the external surface is exposed above the surface of the medium and maintaining the matrix with the skin thereon under skin culturing conditions.

Potentially any skin from any animal can be used in this assay. Preferably, the animal is a mammal. Exemplary mammals are mice, rats, guinea pigs, hamsters, rabbits, marmosets, monkeys and humans. More preferably, the animal is a human.

The skin sample having dermal and epidermal layers is typically excised from an animal. Excess fat, if present, is removed. The sample of skin may be excised from a hairy animal whose skin is capable of supporting hair growth or from a hairless animal whose skin is devoid of hair, such as an athymic, nude animal. Where the skin sample is obtained from a hairy animal, the skin may be shaved or clipped prior to excision.

The skin sample is defined herein as having internal and external surfaces. The phrase “internal surface” refers to the dermally-oriented surface; i.e. the non-exposed surface of the skin as it exists in its native-state in the animal. The phrase “external surface” refers to the epidermally-oriented surface: i.e. the exposed surface of the skin as it exists in its native-state in the animal.

There is no real limitation as to the surface area of a piece of skin used in the present invention. Typically, the skin sample can range in external surface area from about 1 to about 10,000 square millimeters ($mm^2$). A preferred surface area is from about 4 to about 100 $mm^2$. A more preferred surface area is about 10 $mm^2$. The thickness of the skin is a function of the animal from which it is obtained. Where the skin sample is excised from a mouse, a preferred thickness is about 1 to 2 mm.

Skin samples are cultured on a support matrix. A support matrix of this invention provides a trabecular structure with interstices suited for capillary action to deliver aqueous nutrients from the medium to the of internal surface (base) the skin as in a native state. Thus, any support having this capacity is contemplated including synthetic meshes such as nylon, borosilicate glass fiber, or polypropylene or organic meshes such as cellulose or collagen. Preferably, the support matrix is an extracellular support matrix. As used herein, the phrase “extracellular support matrix” means a solid, such as a gel or sponge, comprising one or more organic molecules or molecular aggregates, which molecules or aggregates are those produced and secreted by cells into the extracellular space and which serve, in vivo, as a support, adhesive and framework for maintaining three-dimensional tissue organization and function. Exemplary of such molecules are high-molecular weight proteins and glycoproteins such as collagen, laminin, fibronectin and the like, complex polysaccharides and the like molecules.

In a preferred embodiment, the extracellular support matrix is a collagen-containing gel. Exemplary collagen-containing gels are gelatinized pork skin such as GELFOAM™ (The Upjohn Company, Kalamazoo, Mich.) and a composition comprising laminin, collagen, proteoglycan and entactin such as MATRIGEL™ (Collaborative Research, Inc., Bedford, Mass.). GELFOAM™ is a patented product described in U.S. Pat. No. 2,465,357, the disclosure of which is incorporated herein by reference.

In another preferred embodiment, the extracellular support matrix is a homopolysaccharide sponge. Leighton, J., *J. Nat'l Cancer Instit.,* 12: 545–561 (1951). A preferred homopolysaccharide is cellulose. Homopolysaccharide sponges contemplated by the present invention are not limited as to weave or net size.

In still another preferred embodiment, the extracellular support matrix comprises a combination of a collagen-containing gel and a homopolysaccharide sponge. Preferably, such a combination comprises a top layer of a collagen-containing gel and a bottom layer of a homopolysaccharide sponge. The collagen-containing gel is preferably gelatinized pork skin and the homopolysaccharide is preferably cellulose. In a particularly preferred embodiment, the support matrix comprises a combination of a top layer of GELFOAM™ and a bottom layer of a cellulose sponge, which matrix has been shown to be most effective in maintaining normal hair growth of histocultured skin (see Example 3).

There are no set ratios of skin sample size to size of the extracellular support matrix. The matrix can be anywhere from a diameter which is sufficient to support the skin sample to being greater in size and substantially overlapping the skin sample. Multiple samples can be placed on the same matrix so long as the skin samples are not actually touching. A preferred distance between skin samples is about 1 to 2 mm.

The skin sample is placed on the matrix such that the internal surface of the skin is adjacent to the matrix and the external surface of the skin is facing away from the matrix. In a preferred embodiment, the internal surface of the skin is in contact with the matrix. In this arrangement, the external surface of the skin is available for contacting with toxins or other compositions to assess their effect on the skin according to the present methods.

The matrix with the skin sample thereon is immersed in a volume of a medium sufficient to contact the matrix but not to completely cover the skin; i.e. the external surface of the skin is not submerged but is exposed above the surface of the medium. Preferably, the surface of the medium is within 0.5 to 2 mm of the upper surface of the matrix and provides aqueous contact to the skin sample through a wicking effect. For example, where the skin sample has a thickness of about 1 to 2 mm, the surface of the medium is preferably from about 0.5 to about 2 millimeters below the external surface of the skin.

The extracellular support matrix is typically soft and may indent upon placement of the skin sample thereon such that the edges of the matrix may contact the vertical edges of the skin sample.

The extracellular support matrix is pretreated to equilibrate the matrix with the medium before the skin sample is placed thereon. Pretreatment of the matrix comprises cutting the matrix to a predetermined size and soaking the cut matrix in the medium in a sterile container for a period of time sufficient to saturate and equilibrate the matrix with the medium. A preferred soaking time is 4 hours at 37° C.

The medium contemplated by the present invention is an aqueous nutrient medium designed to promote and maintain viability of the skin sample. A preferred medium is Eagles Minimum Essential Medium (MEM) supplemented with 10% (v/v) fetal bovine serum (FBS) and an antibiotic. Exemplary antibiotics are gentamicin, streptomycin, penicillin, kanomycin and the like. A preferred antibiotic is gentamicin. The final concentration of antibiotic in the medium depends upon the particular antibiotic used. Where the antibiotic is gentamicin, a preferred concentration is about 0.2 mgs per ml of medium. Other mediums can also be used, preferably involving the use of fetal bovine serum, or using serum-free defined mediums as is well known in the art.

The matrix with the skin sample thereon may be maintained in the medium for indefinite periods of time. Preferably, the medium is changed every 2 to 3 days.

One advantage of the skin histoculturing system of the present invention is the provision of a simple, inexpensive, in vitro model whereby the native-state, three-dimensional structure of skin is maintained for long periods of time. In previously described skin culturing systems, skin viability was only maintained for one or two days at best. Kao et al., *Toxicology and Applied Pharmacology,* 81: 502–516 (1985).

Another aspect of the present invention is an extracellular support matrix for use in such a system. In one embodiment, the extracellular support matrix comprises a collagen-containing gel such as GELFOAM™ or MATRIGEL™. In another embodiment, the extracellular support matrix comprises a homopolysaccharide sponge such as a cellulose sponge. In a preferred embodiment, the extracellular support matrix is a combination matrix comprising an upper layer of a collagen-containing gel and a bottom layer of a homopolysaccharide sponge. Most preferred is a combination matrix comprising an upper layer of GELFOAM™ and a bottom layer of a cellulose sponge. Such a matrix has superior qualities for supporting normal hair growth in histocultured mouse skin (see Example 3).

B. Skin Toxicity Assay

Another aspect of the present invention relates to a skin toxicity assay comprising the steps of (a) culturing a skin sample having internal and external surfaces on an extracellular support matrix immersed in a medium under skin culturing conditions whereby the internal surface is adjacent to the matrix and the external surface is exposed above the surface of the medium, (b) contacting the skin sample with a putative toxin, (c) maintaining the skin sample and matrix in the presence of the toxin for a preselected period of time, and (d) assessing the viability of the skin sample and thereby the skin toxicity of the toxin.

Skin samples used for the toxicity assay are preferably devoid of hair. A preferred source of hairless skin is a hairless animal such as an athymic nude animal. An exemplary nude animal is an outbred nude mouse strain derived from Balb/C nude mice.

The extracellular support matrix, medium and culturing conditions for the skin toxicity assay are the same as those set forth above regarding the native-state histoculturing method.

In one embodiment, viability is assessed by measuring the incorporation into cells of the skin sample of an indicator specific for viable cells. As used herein, the phrase "specific for viable cells" means that the indicator is taken up or incorporated into living, but not dead, cells.

The indicator specific for viable cells may be a metabolic precursor or a non-metabolite that gains access to living cells. Exemplary metabolic precursors are ribo- or deoxyribonucleic acid precursors such as purines, pyrimidines, nucleosides and nucleotides. Preferably, the metabolic precursor is operatively linked to an indicating means to facilitate detection. A preferred indicating means for a metabolic-precursor indicator is a radiolabel such as $^{35}S$, $^{32}P$, $^{125}I$, $^{3}H$ and the like. A particularly preferred radiolabeled metabolic-precursor indicator is $^{3}H$-thymidine.

A preferred non-metabolite indicator specific for viable cells is a dye that is capable of optical detection. Any dye recognized in the art as being specific for viable cells can be used in accordance with the skin toxicity assay of this invention. See, e.g., Handbook of Fluorescent Probes and Research Chemicals, ed. by R. P. Haugland, Molecular Probes, publisher, Eugene, Oreg. (1989–1991).

In a preferred embodiment, the dye is a fluorescent dye. Exemplary viable-cell-specific fluorescent dyes are BCECF-AM (B-1150), Calcein-AM (C-1430), CFDA (carboxyfluorescein diacetate; C-195) Acridine orange (A-1301), Calcein blue (H-1426), Fura-2AM (F-1201), Fluorescein diacetate (F-1303) or Carboxy analog (C-1431) and the like. Such dyes are well known in the art and are commercially available (Molecular Probes, Eugene Oreg.). Particularly preferred are the dyes BCECF-AM or Calcein-AM. The numerals in the parenthesis indicates the product number for the listed fluorescent dyes that are available from Molecular Probes.

In one embodiment, the incorporation or uptake of fluorescent dyes specific for viable cells depends upon metabolic activity of the viable cell. In accordance with this embodiment, non-fluorescing dyes are taken up by viable cells and converted to a fluorescing product by an intracellular enzyme such as an esterase. The presence of intracellular fluorescence indicates viability.

In another embodiment, viability is assessed by measuring the uptake or incorporation into cells of the skin sample of an indicator specific for dead cells. As used herein, the phrase "specific for dead cells" means that the indicator is taken up or incorporated only into dead, non-viable cells.

Typically, dyes specific for dead cells are compounds with a high ionic charge and low permeability such that the dyes cannot permeate intact cellular membranes. When cells die, the membrane is structurally or functionally ruptured such that dyes specific for dead cells gain access to the intracellular space where they bind to intracellular components such as nuclear membranes.

A preferred dead-cell-specific indicator is a dye capable of optical detection. A preferred dead-cell-specific dye is a fluorescent dye such as propidium iodide, ethidium bromide, ethidium homodimer [(5,5'-diazadecamethylene) bis (3,8-diamino-6-phenyl-phenanthridium) dichloride, dihydrochloride] and the like. Most preferred is propdidium iodide. Propidium iodide (PI) and other dyes specific for dead cells are well known in the art and commercially available (Molecular Probes, Eugene, Oreg.).

In still another preferred embodiment, assessing viability is accomplished by simultaneously measuring the uptake or incorporation of both an indicator specific for viable cells and an indicator specific for dead cells. Viability is assessed as the ratio of viable to dead cells. Where both the indicator specific for viable cells and the indicator specific for dead cells are fluorescent dyes, such dyes should have different emission spectra so as to facilitate discrimination between viable and dead cells. Compositions and methods for determining cell viability by the differential uptake of indicators specific for viable and dead cells and tissue culture samples are well known in the art. Haughland, Supra.

In a preferred embodiment, the skin toxicity assay further comprises assessing the viability of the skin sample prior to contacting the skin sample with a putative toxin and comparing the assessed viability before and after contact with the putative toxin and thereby determining the toxicity of the toxin.

Means for detecting the uptake or incorporation of indicators specific for viable cells are dependent upon the particular indicator used and are well known to those of skill in the art. A preferred means for detecting radiolabeled metabolic-precursors is autoradiography of histological sections of the skin samples that have taken up the precursor.

A preferred means for detecting dyes is microscopic examination. Microscopic examination can involve the use of any microscope that allows one to selectively and reproducible evaluate indicator incorporation into specific cells of the skin sample at varying locations within the three-dimensional, native- state skin histoculture.

Typically, the microscopic examination requires the capability of optical sectioning. Optical sectioning is the ability to view preselected depths within the three-dimensional structure of the skin in the absence of optical interference provided by the presence in the skin of microsomes, air bubbles, fat globules and other tissue components, which provide reflection of light and optical interference.

In addition, optical sectioning allows for viewing a variety of planes within the three-dimensional skin histoculture. By sequentially sectioning serial layers of the skin, one can produce a total picture of the skin or, alternatively, a picture of a region of the skin where a particular cell type of interest is located. Thus, comparative studies of a plurality of depths or regions of the skin can be made. In this way, viability can be assessed in surface cells, at cells underneath the dermal layer, cells inside the epidermal layer, or in other specific cell types such as nerve cells, oil secreting cells, hair follicle cells.

The optical section thickness can be varied to accomodate the cell size or tissue to be observed and can range from about 0.1 to 1000 microns. Preferred sections are in the range of 0.5 to 10 microns, preferably about 2 to 6 microns.

A preferred microscope that is capable of performing optical sectioning is a confocal scanning laser microscope such as the MRC-600 CONFOCAL IMAGING SYSTEM (Bio-Rad, Richmond, Calif.), mounted on a Nikon Optiphot using a 10× PlanApo plan objective. Such a confocal scanning microscope has been successfully used to study skin toxicity (see Examples 1 and 2). Other available methods for optically scanning or sectioning planes of the tissue sample are also contemplated by the present invention.

Viability is assessed at any particular location within the skin as a ratio of viable or dead cells to total cells or as a ratio of live to dead cells on the basis of the uptake of indicators specific for viable and dead cells respectively. When viability is assessed both before and after contact with a putative toxin, comparing the ratio of live to dead cells as assessed before and after contact with the putative toxin provides an indication of the toxicity of the putative toxin.

The procedure for applying indicators to the skin culture varies with the particular indicator used. Typically, indicators are added to the medium about 6 hours and, preferably about 24 hours after placing the skin sample in the medium. Following addition of the indicator to the medium, the culture is maintained under culturing conditions for a period time sufficient to allow the indicator to enter and label the cells of the skin sample. Preferably, the culture is maintained in the presence of the indicator for about 5 minutes to about 2 hours and, more preferably for about 10 to 20 minutes.

The concentration of indicator added to the medium varies with the particular indicator used. Where the fluorescent dyes PI and BCECF-AM are used, the dye concentration is from about 1 to about 100 micromolar, preferably from about 2 to about 50 micromolar, and more preferably about 5 micromolar each.

Typically the skin sample is contacted with the putative toxin by adding the toxin directly to the medium. Alternatively, the toxin is added directly to the surface of the skin sample. After addition of the toxin, the skin sample is maintained in the toxin-containing medium for a preselected period of time, which time varies with the particular toxin being studied.

The skin toxicity assay of the present invention provides advantages and benefits over presently available methods for toxicity testing. One major advantage relates to the provision of a reliable, in vitro assay that obviates the exposure of live animals to toxic substances. Thus, the present assay can be used to replace traditional forms of skin toxicity testing such as the Draize test.

C. Hair Growth Assay

In yet another aspect, the present invention relates to a hair growth assay comprising placing a skin sample having internal and external surfaces on an extracellular support matrix immersed in a medium whereby the internal surface is adjacent to the matrix and the external surface is exposed above the surface of the medium, maintaining the matrix with the skin thereon in the medium under skin culturing conditions and assessing the growth of hair in the skin.

For the hair growth assay, the skin sample is obtained from a hairy animal and therefore the skin sample contains hair cells, including the normal complement of tissue components for supporting hair growth including a hair follicle hair shaft and the like structures typically found in the skin surrounding the hair shaft. Preferably, the skin sample contains multiple hair shafts. A particularly preferred animal is a baby animal. In a preferred embodiment, skin is excised from the dorsal back, neck or scalp, although any skin supporting hair growth maybe used. The skin sample is shaved or clipped prior to excision from the animal. Other methods of removing the hair can be used with the limitations that the hair follicle is not removed from the skin and the base of the hair shaft is not removed from the follicle.

The nature of the extracellular support matrix, the composition of the medium and the culturing conditions are substantially the same as defined above with respect to the histoculturing system and the skin toxicity assay.

The hair growth assay comprises the steps of (a) culturing a skin sample obtained from a hairy animal and having internal and external surfaces on an extracellular support matrix immersed in a medium whereby the internal surface is adjacent to the matrix and the external surface is exposed above the surface of the medium, (b) making a first determination of hair growth status, (c) maintaining the skin sample and matrix in the medium for a preselected period of time, (d) making a second determination of hair growth status and (e) comparing the first and second determinations of hair growth status thereby determining hair growth.

As used herein, the phrase "hair growth status" refers to any parameter indicative of hair growth. Preferably, such a parameter is a physical dimension of the hair and, more preferably hair length or diameter. Means for determining hair growth status depend upon the particular parameter studied. Where the parameter is hair length, length is determined in situ on the histocultured skin sample. Where the parameter is hair diameter, diameter is determined in situ using microscopic enhancement of the hair shaft or in vitro using photomicrographs of histologically sectioned hair shafts. Assays for assessing hair growth are well known in the art. Fraiter et al., *J. Invest. Dermatol.,* 61:72–81 (1973).

In addition to providing an in vitro means for measuring growth, the present assay has utility for evaluating the effects of putative hair growth stimulants. In this embodiment, an initial determination of hair growth status is made on a histocultured skin sample, a putative hair growth stimulant is contacted with the skin sample, the skin sample is maintained in the presence of the stimulant for a predetermined period of time, a second assessment of hair growth status is made and a comparison of changes in hair growth in the presence and absence of such agents is made. Such an embodiment has great utility, for example, in testing the hypertrichosis effects of drugs such as minoxidil, diazoxide and the like.

Alternatively, the hair growth assay can be modified to study characteristics of hair other than growth. For example, the assay can be used to test the efficacy and safety of compositions, such as dyes, designed to alter hair color. The present assay and modifications thereof provide manufacturers of compounds designed to affect hair growth or quality the opportunity to test their compounds in vitro prior to experimentation with live animals such as humans.

D. Anti-Aging/Anti-Wrinkling Assays

The native-state skin histoculturing system of present invention also has application to assays for evaluating the anti-aging or anti-wrinkling effects of putative anti-aging or anti-wrinkling agents. For such assays, the extracellular support matrix, the medium and the skin culturing conditions are substantially the same as described above in reference to the skin toxicity assay. Skin samples used in the anti-aging or anti-wrinkling assay, however, may be obtained from either hairy or hairless animals.

In the anti-aging assay, a parameter indicative of skin age is assessed. Exemplary age-indicative parameters include thickness of the epidermis (the epidermis thins with age), melanin content of the epidermis (melanin content decreases with age) and epidermal gland number (the number decreases with age). Cecil Textbook of Medicine, 15th Edition ed. by Beeson et al., W. B. Saunders, Philadelphia, pp. 27 and 2272, (1979).

In the anti-wrinkling assay, parameters indicative of wrinkling are assessed. Exemplary wrinkling-indicative parameters include collagen and elastin content (both of which decrease in association with increased wrinkling), skin elasticity and physical parameters such as the frequency and distribution of epidermal folds. Textbook of Medicine, supra.

In one embodiment of the anti-aging and anti-wrinkling assays, the skin sample is obtained from a aged animal donor where the skin exhibits signs of wrinkling or aging, and the putative anti-aging or anti-wrinkling agents are studied for their ability to reverse or attenuate the aging or wrinkling process.

In another embodiment, the skin sample is obtained from a young animal and the putative anti-aging or anti-wrinkling agents are tested for their ability to prevent aging or wrinkling.

The anti-aging or anti-wrinkling assays of the present invention have a number of utilities and applications. The assays are used to test the effects of cosmetics such as moisturizers, carriers, emollients, emulsifiers and the like.

In one embodiment, numerous parameters of the skin sample can be assessed before and after treatment with test agents. In this way, data concerning the effects of various agents on aging, wrinkling, toxicity and hair growth can be evaluated simultaneously in the same histoculturing system.

The following Examples serve to illustrate particular embodiments of the invention and are not limiting of the specification and claims in any way.

EXAMPLES

1. A Native-State Skin Histoculture

Samples of skin having an external surface area of about 10 $mm^2$ and a thickness of about one to two mm were excised from an athymic nude mouse and placed on a GELFOAM™ matrix immersed in Eagle's MEM containing about 0.2 mg/ml of gentamycin and about 10% (v/v) fetal bovine serum. Prior to use the matrix was soaked in the medium for four hours at 37° C. to equilibrate the matrix in the medium.

Figure 2:
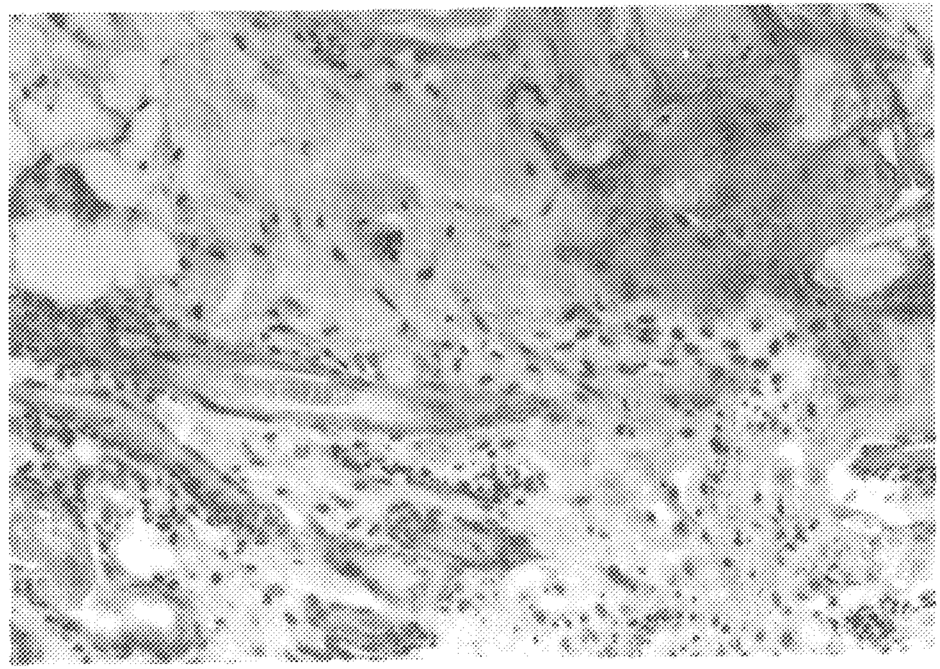
FIG. 2 is a colored photomicrograph depicting mouse skin histocultured for 6 days in Eagles MEM and labeled with [$^3$H]-thymidine for days 3–6. Skin was fixed and processed for autoradiography and stained with hematoxylin and eosin as described in Example 1. Autoradiograms were observed with bright-field and polarizing light. [$^3$H]-thymidine-labeled nuclei appear bright green. Magnification 1000×.

The skin samples were maintained on the matrix in the medium at a temperature of about 37° C. in a gassed incubator under a mixture of 95% air and 5% $CO_2$. Viability of the cultured skin samples was assessed at various times after initiation of the culture as indicated in FIGS. 1 and 2. Viability was assessed as the uptakes of an indicator specific for viable cells (BCECF-AM) and an indicator specific for dead cells (propidium iodide, PI), or as the uptake of [$^3$H]-thymidine.

The fluorescent dye indicators BCECF-AM and PI (Molecular Probes, Eugene, Oreg.) were added directly to the medium at a final concentration of 5 micromolar. Incorporation of the dyes was microscopically evaluated about 30 min following addition of the dyes to the medium by optical scanning using an MRC-600 Confocal Imaging System (Bio-Rad, Richmond, Calif.) mounted on a Nikon Optiphot equipped with a 10× PlanApo Objective. Samples were observed using an optical section of about 4 microns. [$^3$H]-Thymidine was added directly to the medium at a final concentration of 4 $\mu$Ci/ml. Skin samples were maintained in the thymidine-containing medium for 3 days. After the 3 days, the skin cultures were washed with phosphate-buffered saline, pH 7.0, placed in histology capsules and fixed in 10% (v/v) formalin. The fixed skin cultures were then dehydrated, embedded in paraffin, sectioned and placed on slides by standard methods well known to those of skill in the histology art. The slides were deparaffinized, coated with Kodak NTB-2 emulsion, exposed for 5 days and developed. See, e.g. Freeman et al., *Proc. Soc. Natl. Acad. Sci. USA,* 83:2694–2698 (1986) and Hoffman et al., *Proc. Soc. Acad. Sci. USA,* 86:2013–2017 (1989). The developed slides were rinsed, stained with hematoxylin and eosin and examined using a Nikon or Olympus photomicroscope fitted with epi-illumination polarization.

The results of these studies are shown in FIGS. 1 and 2.

As shown in FIG. 1, mouse skin histocultured on a floating GELFOAM™ matrix in Eagle's minimum essential medium for 2 days demonstrated a preservation of native-state, three-dimensional tissue architecture of all major cell types. The hair follicles, epidermal cells and dermal fibroblasts were readily visualized by confocal microscopy as having incorporated BCECF-AM (green-live cells) but not PI (red-dead cells) and appear to have normal morphology. The skin histocultures were viable for at least 10 days.

As shown in FIG. 2, cells in the skin histoculture retained their proliferative activity for up to 6 days. DNA synthesis and replication, shown by histological autoradiography using polarizing photomicroscopy ([$^3$H]-thymidine labeled nuclei are bright green), was evident in hair follicles, epidermal, and dermal cells. The percentages of [$^3$H]-labeled cells for the follicle, epidermal, and dermal cells were 38.6%, 75.2%, and 10.2%, respectively.

These data demonstrate that skin samples remain viable for at least several days when histocultured on a GELFOAM™ matrix in Eagle's MEM.

2. Skin Toxicity Assay

Skin samples from athymic nude mice were cultured according to the method of Example 1. Viability was assessed before and after the addition of putative toxins using BCECF-AM and [$^3$H]-thymidine as indicators specific for viable cells and PI as an indicator specific for dead cells. The uptake of these indicators was determined according to the methods of Example 1.

An initial assessment of viability was made 2 days after initiation of the skin culture using BCECF-AM and PI. Immediately following this initial assessment, various concentrations of the toxins ethanol, doxorubucin or sodium hypochlorite were contacted with the skin samples. The final concentrations of the toxins varied from about 0.5% to about 70% (v/v) for ethanol, from about 29 to about 725 mgs/ml for doxorubicin and from about 0.6% to about 60.0% (v/v) for sodium hypochlorite.

The skin samples were contacted with ethanol, doxorubicin and sodium hypochlorite for about 5 min., for about 24 hours and for about 2 hours respectively. Following these contact times, the toxin-containing medium was replaced with fresh, non-toxin-containing medium and the skin samples reassessed for viability using BCECF-AM and PI. Viability was assessed in the same region of the skin sample before and after contact with the toxin.

In addition, skin samples contacted with doxorubicin were assessed for viability using the uptake of [$^3$H]-thymidine measured after 24 hr of toxin contact.

The results of these studies are summarized in FIGS. 3–7.

Figure 3:
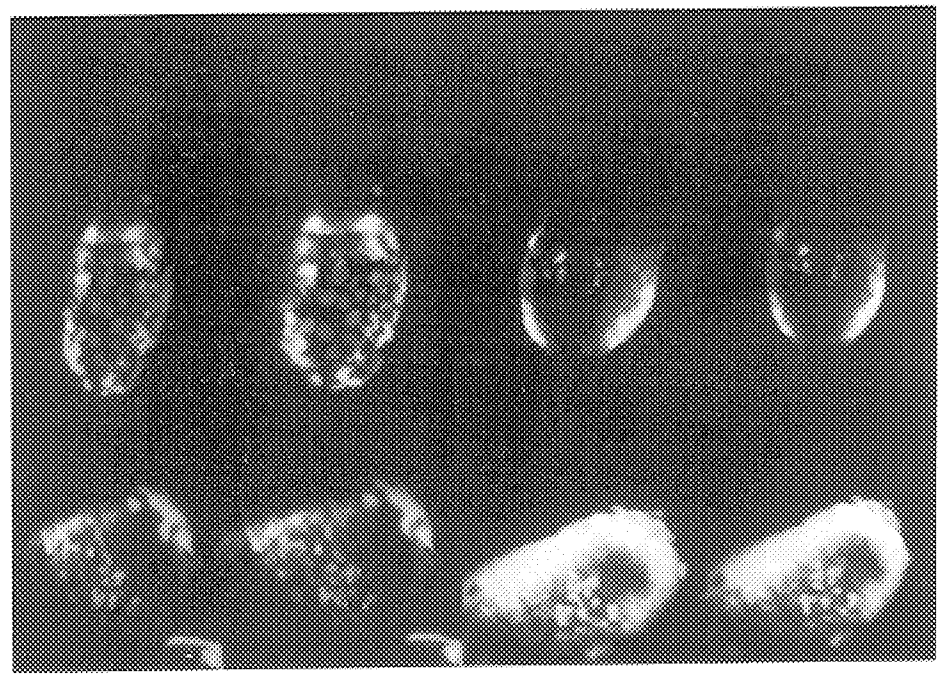
FIG. 3 is a colored photomicrograph depicting the viability of hair follicles of mouse skin histocultured for 2 days and double stained with BCECF-AM (green-live cells) and PI (red-dead cells) following exposure to ethanol as described in Example 2. Left-hand images show skin before ethanol treatment; right-hand images show skin after treatment. Top images show skin exposed to 0.5% (v/v) ethanol treatment. Bottom images show skin exposed to 5.0% (v/v) ethanol treatment. Confocal scanning laser microscopy. Magnification 100×. Stereo Image.

FIG. 3 is a colored photomicrograph of histocultured mouse skin before and after treatment with ethanol. The toxicity of ethanol was determined by assessing the viability of the skin sample before and after treatment with ethanol and comparing the two viability assessments. In accordance with the assessment of viability described above in Example 1, viable cells are stained green, while dead cells are stained red. The photomicrographs show that before ethanol treatment (left-hand images) the vast majority of cells in the mouse skin were viable. Following treatment with either 0.5% (v/v) (top right-hand images) or with 5.0% ethanol (bottom right-hand images) a large number of cells died. The data further show that 5.0% ethanol was more toxic (a greater loss in viability) than was 0.5% ethanol. Results using 30%, 50% and 70% ethanol, showed increasing losses of viability above the extent of losses observed using 5% ethanol (data not shown).

Figure 4:
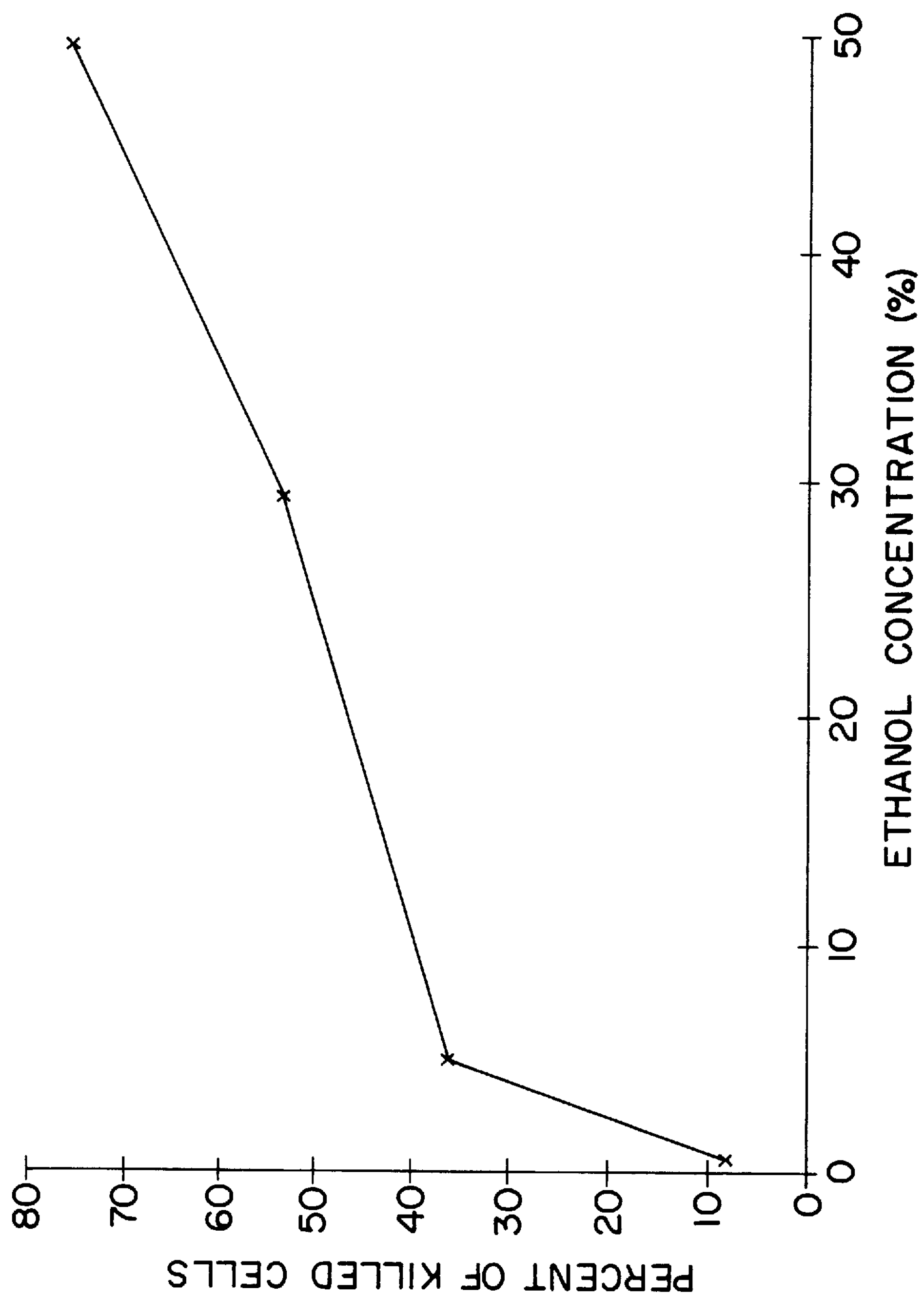
FIG. 4 is a graphical depiction of the dose-dependent toxic effects of ethanol on viability of mouse skin histocultured for two days. Toxicity was assessed as the relative uptakes of BCECF-AM and propidium iodide (PI) after ethanol treatment for 5 minutes and is expressed as the percent of killed cells as a function of ethanol concentration as described in Example 2.

The data in FIG. 4 show the dose-dependent toxic effects of ethanol on histocultured mouse skin. In this study, toxicity was expressed as a percent of killed cells. The fraction of killed cells (PI-positive cells) with respect to total cells [PI-positive (red) plus BCECF-AM-positive (green) cells] in treated cultures is measured with confocal flourescence scanning microscopy and is compared to untreated controls to determine cytotoxicity. The percent of killed cells is expressed as the number of red cells after treatment minus the number of red cells before treatment, divided by the total number of cells (green cells after treatment plus red cells after treatment). The data show that the percent of killed cells (toxicity) increases as the concentration of ethanol increases.

The effects of doxorubicin and sodium hypochlorite on skin toxicity were determined in an identical manner to that described above for ethanol.

Figure 5:
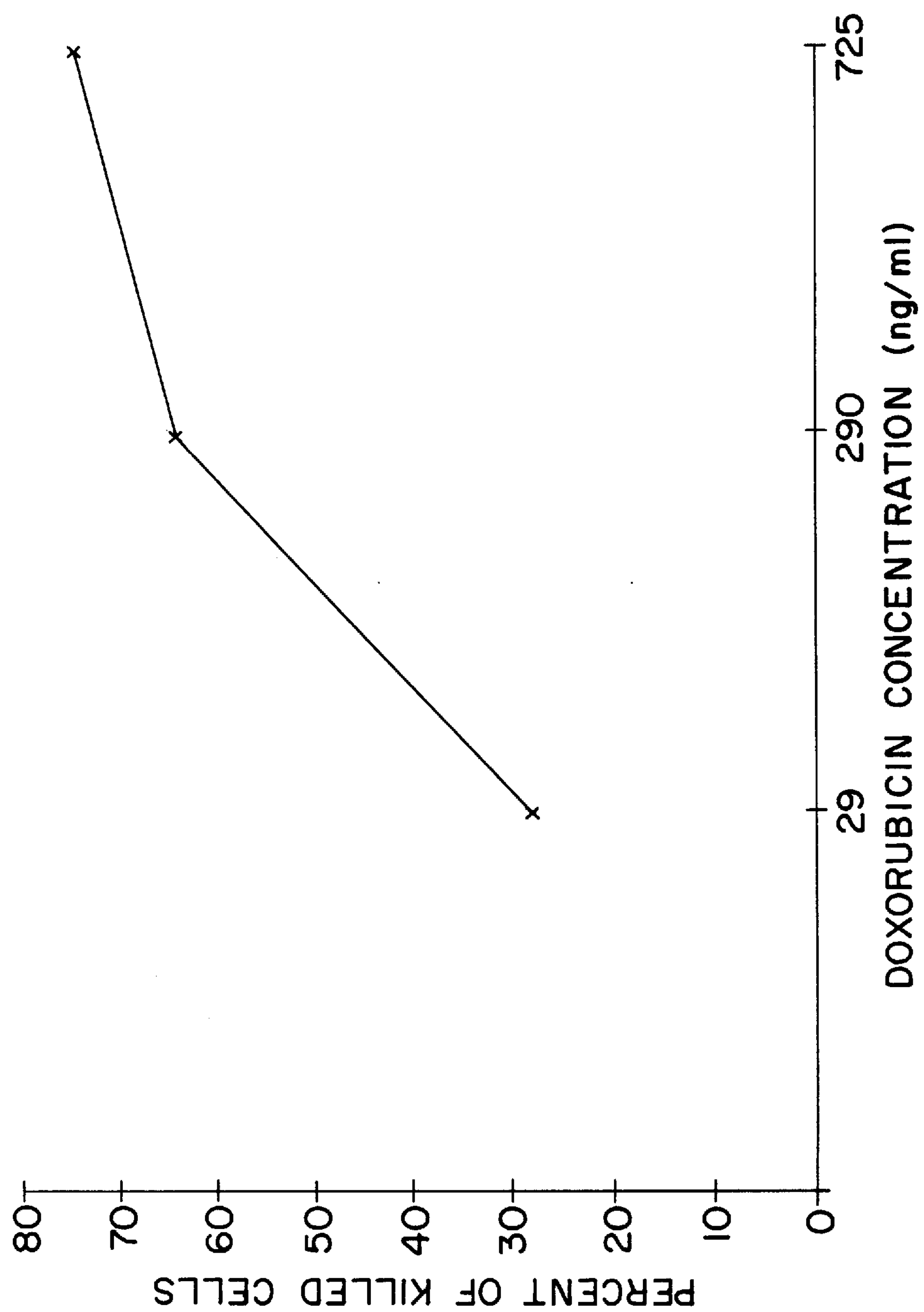
FIG. 5 is a graphical depiction of the dose-dependent toxic effects of doxorubicin on viability of mouse skin histocultured for 4 days. Toxicity was assessed as the relative uptake of BCECF-AM and PI staining after doxorubicin treatment for 24 hours and is expressed as the percent of killed cells as a function of doxorubicin concentration as described in Example 2.

The data in FIG. 5 show the dose-dependent toxic effects of doxorubicin on histocultured mouse skin. The data show that the toxicity of doxorubicin was relatively proportional to the concentration of doxorubicin added to the histoculturing system.

Figure 6:
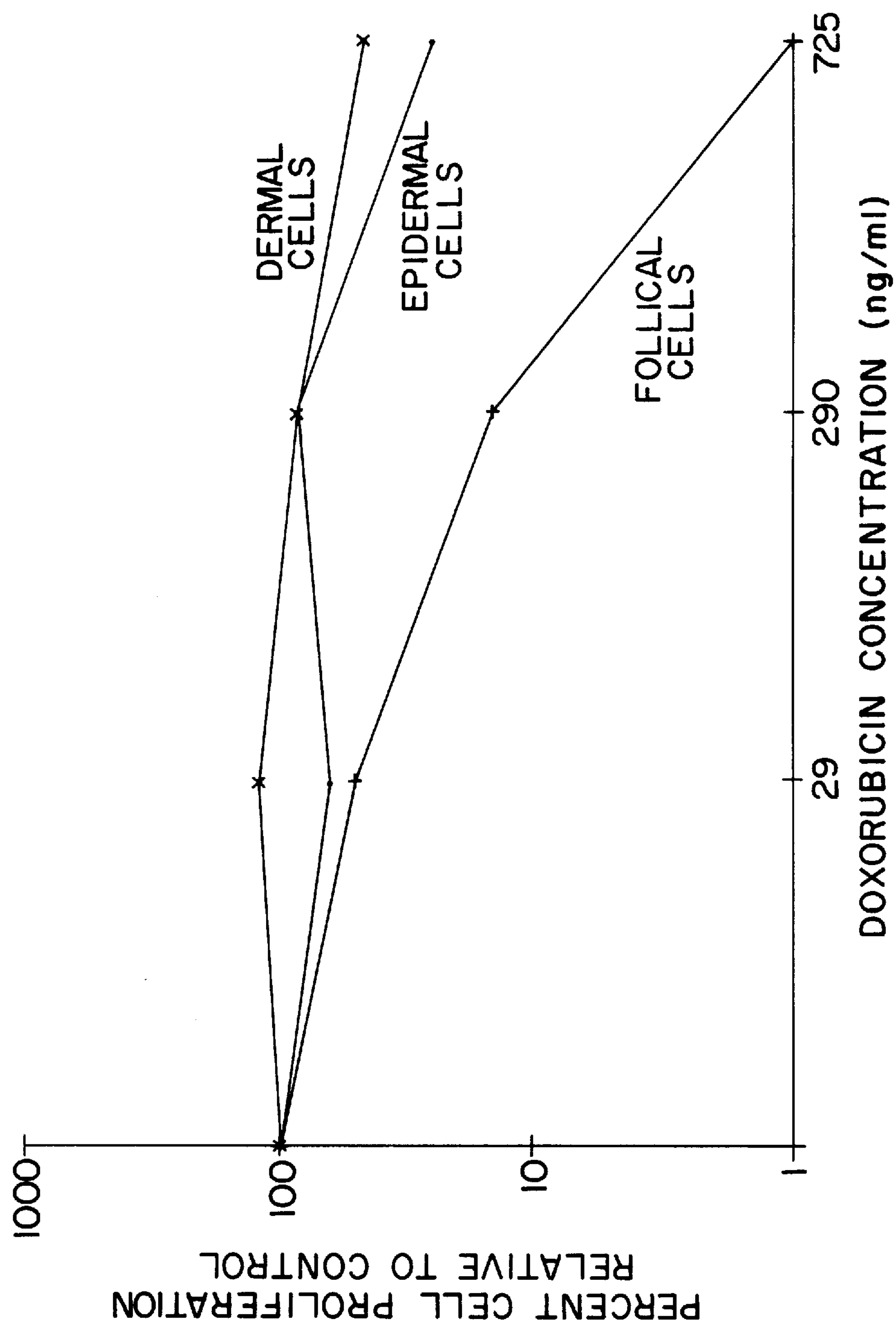
FIG. 6 is a graphical depiction of the dose-dependent toxic effects of doxorubicin on viability of different cell types in mouse skin histocultured for 2 days. Toxicity was assessed as the uptake of [$^3$H]-thymidine after doxorubicin treatment for 24 hours. The percent of cell proliferation was calculated as the percent of labelled cells in doxorubicin-treated skin relative to the percent of labelled cells in control, non-treated skin.

The data in FIG. 6 show the dose-dependent toxic effects of doxorubicin on various cell types within a native-state histocultured mouse skin namely, the dermal cells, the epidermal cells and the follical cells. A 24 hour exposure of histocultured mouse skin to doxorubicin inhibited DNA synthesis in skin cells in a dose-dependent fashion. In this study, toxicity was expressed as percent cell proliferation. Percent cell proliferation was calculated as the ratio of, (1) percentage of cells labeled with [$^3$H]-thymidine to total cells in doxorubicin treated samples compared to (2) the percentage of [$^3$H]-thymidine labeled cells to total cells in control, untreated skin samples. Relative to controls, doxorubicin treatment resulted in a dose-dependent decrease in cell proliferation. The data also show that the effects of doxorubicin varied with particular cell types. The toxicity of doxorubicin was most pronounced in hair follicle cells.

Figure 7:
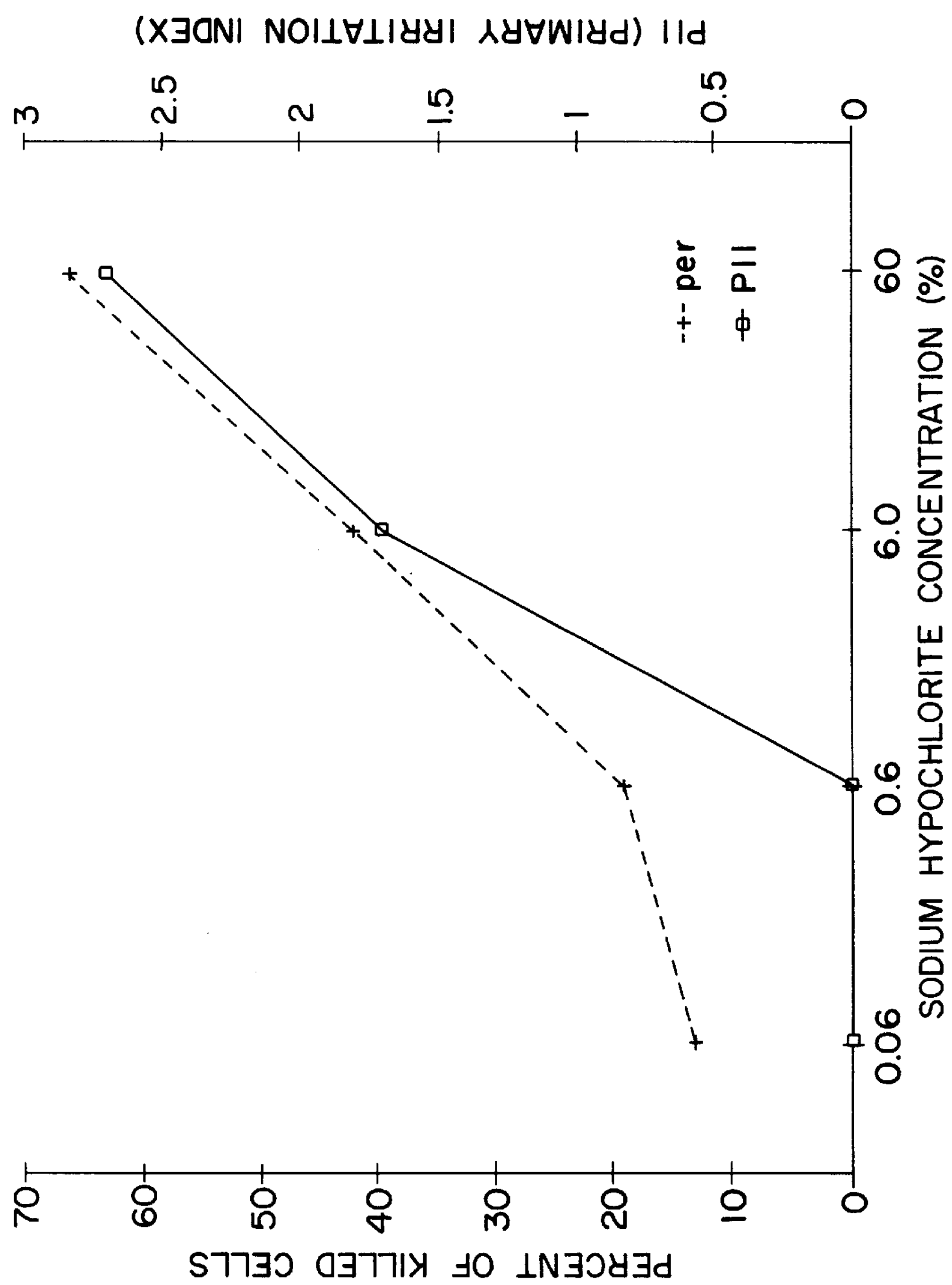
FIG. 7 depicts the dose-dependent toxic effects of sodium hypochlorite on viability of histocultured mouse skin and on the in vivo irritation of mouse skin. Toxicity is expressed as a percentage of killed cells (per), and as a primary irritation index (PII), both as a function of sodium hypochlorite concentration as described in Example 2.

FIG. 7 shows comparative studies that were performed to evaluate the reliability of skin toxicity assessments using the in vitro histocultured skin samples of the present invention when compared to skin toxicity assessments made in vivo. The in vivo assessment of toxicity was determined using a standard skin irritation test as set forth below.

Small pieces of gauze paper (about 1.5 cm$^2$ size), which have been soaked in different concentrations of sodium hypochlorite, were tightly put on 3 different sites on the dorsal surface of the mice. Skin sites were scored on a 1 to 4 scale for erythema and edema ½ hour and 1 hour after removal of the sodium hypochlorite. The primary irritation index (PII) for each concentration of sodium hypochlorite was derived from the following formula:

$$PII = \frac{\text{Total score (erythema and edema)}}{\text{Number of sites} \times \text{Number of observations}}$$

The results of this study are summarized in FIG. 7.

The data in FIG. 7 show a high positive correlation between toxicity assessed in vivo and in histocultured mouse skin. In particular, the data show that the threshold of toxicity (about 0.6% sodium hypochlorite) was identical in the two systems.

These data show that the skin toxicity assay of the present invention can be used to reliably and accurately evaluate the effects of putative toxins.

3. Hair Growth Assay

Skin samples from hairy mice were histocultured in accordance with the method of Example 1 using three different formulations of the extracellular support matrix. The three formulations of the extracellular support matrix were: a GELFOAM™ matrix, a combination matrix comprising an upper layer of MATRIGEL™ and a bottom layer of a cellulose sponge and a combination matrix comprising an upper layer of GELFOAM™ and a bottom layer of a cellulose sponge.

Hair growth was assessed as changes in hair length over six days of histoculturing. For comparison purposes, hair growth was also measured in vitro over the same six day period. The results of this study are summarized in FIG. 8.

Figure 8:
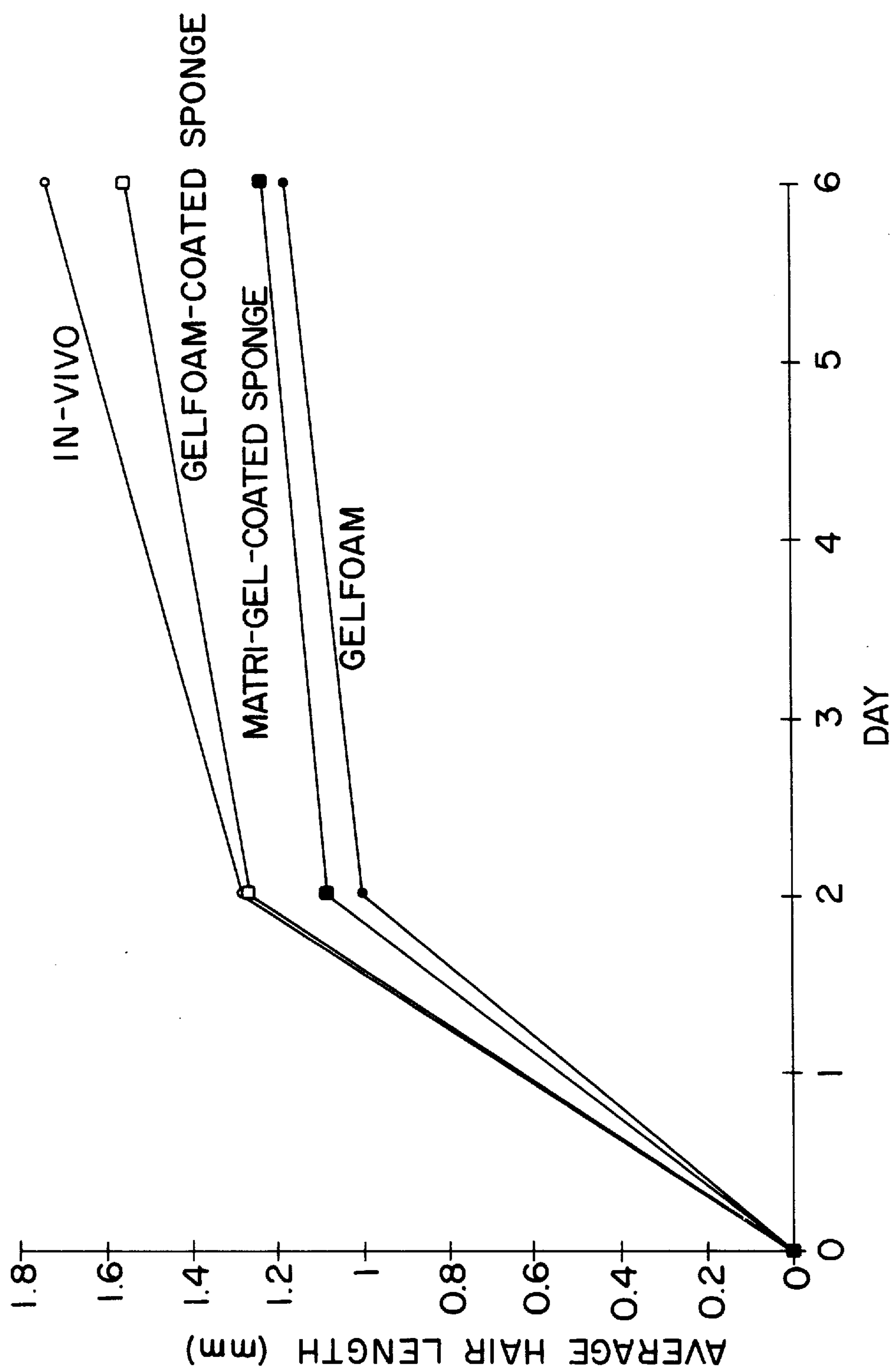
FIG. 8 is a graphical depiction comparing hair growth in the histocultured mouse skin system using several matrices to hair growth in skin in vivo as described in Example 3.

The data in FIG. 8 show that histocultured mouse skin supported normal rates of hair growth. Hair growth of histocultured skin samples most closely approximated the in vivo growth rate when samples of skin were histocultured on a combination matrix comprising an upper layer of GELFOAM™ and a bottom layer of a cellulose sponge.

These data, taken together with the data from Examples 1 and 2, demonstrate that skin samples histocultured in accordance with the methods of the present invention (1) maintain normal native-state, three-dimensional architecture, (2) remain viable for several days, (3) demonstrate cellular proliferation and (4) support normal hair growth. In addition, these data demonstrate that such a histoculturing method provides reliable in vitro assays for skin toxicity and hair growth.

Although the present invention has now been described in terms of certain preferred embodiments, and exemplified with respect thereto, one skilled in the art will readily appreciate that various modifications, changes, omissions and substitutions may be made without departing from the spirit thereof.

What is claimed is:

1. A histoculturing method comprising placing an intact whole skin sample containing hair follicles, said skin sample excised from an animal under conditions wherein the hair follicle is not removed from the skin and the base of the hair shaft is not removed from the follicle, said skin sample having an internal and an external surface on a sponge support matrix immersed in a medium whereby the internal surface is adjacent to the matrix and the external surface is exposed above the surface of the medium, maintaining the matrix with the skin sample thereon in the medium under skin histoculturing conditions which permit hair growth and optionally, assessing the hair growth.

2. A hair growth assay comprising the steps of:

a) culturing an intact whole skin sample containing hair follicles, said skin sample excised from an animal under conditions wherein the hair follicle is not removed from the skin and the base of the hair shaft is not removed from the follicle, said skin sample having an internal and an external surface on a sponge support matrix immersed in a medium whereby the internal surface is adjacent to the matrix and the external surface is exposed above the surface of the medium;

b) making a first measurement of hair growth status;

c) maintaining the skin sample and matrix in the medium for a preselected period of time under histoculturing conditions which permit hair growth;

d) making a second measurement of hair growth status; and e) determining the difference between the first and second measurements of hair growth status thereby measuring hair growth.

3. The assay according to claim 2 wherein hair growth status is a physical dimension of the hair.

4. The assay according to claim 3 wherein the sponge support matrix comprises a collagen-containing gel.

5. The assay according to claim 4 wherein the collagen-containing gel is gelatinized pork skin.

6. The assay according to claim 2 wherein the physical dimension is hair length.

7. The assay according to claim 2 wherein the sponge support matrix is a homopolysaccharide sponge.

8. The assay according to claim 7 wherein the homopolysaccharide is cellulose.

9. The assay according to claim 2 wherein the sponge support matrix comprises a top layer of a collagen-containing gel and a bottom layer of a homopolysaccharide sponge.

10. The assay according to claim 9 wherein the collagen-containing gel is gelatinized pork skin and the homopolysaccharide is cellulose.

11. The assay according to claim 2 wherein the sample of skin is of human origin.

12. The assay according to claim 2 further comprising the step of shaving the skin prior to culturing.

13. The method of claim 2 which comprises the additional step, after step b) and before step c) of contacting said skin sample with a drug or composition.

* * * * *